(12) United States Patent
Tan et al.

(10) Patent No.: US 9,329,279 B2
(45) Date of Patent: May 3, 2016

(54) METHOD AND DEVICE FOR MEASURING RADON BY ELECTROSTATIC COLLECTION METHOD WITHOUT INFLUENCE OF ENVIRONMENTAL TEMPERATURE AND ENVIRONMENTAL HUMIDITY

(71) Applicant: Hengyang Normal University, Hengyang, Hunan (CN)

(72) Inventors: Yanliang Tan, Hunan (CN); Hongzhi Yuan, Hunan (CN)

(73) Assignee: Hengyang Normal University, Hengyang, Hunan (CN)

( * ) Notice: Subject to any disclaimer, the term of this patent is extended or adjusted under 35 U.S.C. 154(b) by 132 days.

(21) Appl. No.: 14/355,447

(22) PCT Filed: May 13, 2013

(86) PCT No.: PCT/CN2013/075531
§ 371 (c)(1),
(2) Date: Apr. 30, 2014

(87) PCT Pub. No.: WO2014/114038
PCT Pub. Date: Jul. 31, 2014

(65) Prior Publication Data
US 2015/0102228 A1    Apr. 16, 2015

(30) Foreign Application Priority Data

Jan. 25, 2013  (CN) ...................... 2013 1 0030195 A (51) Int. Cl.
*G01T 1/167*    (2006.01)
*G01N 15/10*    (2006.01)
(Continued)

(52) U.S. Cl.
CPC ............ *G01T 1/167* (2013.01); *G01N 15/0606* (2013.01); *G01N 15/0656* (2013.01); *G01N 15/10* (2013.01); *G01T 1/178* (2013.01); *G01N 1/24* (2013.01); *G01N 2015/0046* (2013.01)

(58) Field of Classification Search
CPC ................................ G01T 1/167; G01N 15/10
See application file for complete search history.

(56) References Cited

U.S. PATENT DOCUMENTS 5,153,520 A * 10/1992 Dumbeck .......... G01N 33/0024
250/384
6,288,400 B1    9/2001 Negro et al.

FOREIGN PATENT DOCUMENTS

CN        102043159 A    5/2011
CN        102176044 A    9/2011
(Continued)

OTHER PUBLICATIONS

Mechanism analysis to influence of temperature and humidity to device for measuring radon by electrostatic collection method, Ma et al., Nuclear Electronics & Detection Technology, Apr. 2012, p. 482-484.

(Continued)

*Primary Examiner* — David Porta
*Assistant Examiner* — Faye Boosalis (57) ABSTRACT

A method and device for measuring radon by the electrostatic collection method without the influence of the environmental temperature and humidity is by reducing the pressure that in a electrostatic collection and measuring chamber to below a certain threshold value, in the operating temperature range of 0-45 degrees, and the air relative humidity of the external environment changing in 0%-400%, the collection efficiency of the collection and measuring chamber of the static electricity that collects positively charged $^{218}$Po particle to the surface of a semiconductor detector is basically unchanged, so when the temperature and humidity of the external environment change, the detection efficiency does not change; the threshold value relates to the geometric factor and the distribution of the electric field intensity that in different measuring chamber. The device comprises a measuring chamber, a semiconductor detector, a high-voltage module, a sampling pump, a vacuum gauge, and a regulating valve.

5 Claims, 3 Drawing Sheets

(51) Int. Cl.
*G01T 1/178* (2006.01)
*G01N 15/06* (2006.01)
*G01N 1/24* (2006.01)
*G01N 15/00* (2006.01)

(56) References Cited

FOREIGN PATENT DOCUMENTS

| CN | 102636479 A | 8/2012 |
| CN | 103018765 A | 4/2013 |
| EP | 0398980 A1 | 11/1990 |
| GB | 2106641 A | 4/1983 |
| WO | 2010004366 A1 | 1/2010 |

OTHER PUBLICATIONS

Design and Implementation of Air Radon Monitor in α Energy Spectrum Based on Static Electricity Accumulation Method, Qiu Huang, Master Thesis, Chengdu Univerisity of Technology, 2010.

* cited by examiner

METHOD AND DEVICE FOR MEASURING RADON BY ELECTROSTATIC COLLECTION METHOD WITHOUT INFLUENCE OF ENVIRONMENTAL TEMPERATURE AND ENVIRONMENTAL HUMIDITY

CROSS REFERENCE OF RELATED APPLICATION

This is a U.S. National Stage under 35 U.S.C 371 of the International Application PCT/CN2013/075531, filed May 13, 2013, which claims priority under 35 U.S.C. 119(a-d) to CN 201310030195.X, filed Jan. 25, 2013.

BACKGROUND OF THE PRESENT INVENTION

1. Field of Invention

The present invention relates to the field of nuclear radiation detection technology, and more particularly to a method and a device for measuring radon by an electrostatic collection method without the influence of environmental temperature and environmental humidity.

2. Description of Related Arts

Radon ($^{222}$Rn) in the environment is the main source of the natural radiation that is suffered by human There are various methods and various devices for measuring radon based on different principles of measurement. The radon monitor based on an electrostatic collection method is applied widely, due to high degree of automation and the ability of distinguishing energy spectrum to exclude the interference of $^{220}$Rn. The radon monitor based on the electrostatic collection method has a semiconductor detector provided on an upper portion of the measuring chamber; a high voltage is added between the wall of the measuring chamber and the semiconductor detector to form an measuring chamber to form positively charged $^{218}$Po; the positively charged $^{218}$Po is collected to the surface of the semiconductor detector under the function of the electrostatic field. In the process of collecting, the positively charged $^{218}$Po collides with molecule and ion in the air; if the positively charged $^{218}$Po collides with negatively charged ion OH—, the positively charged $^{218}$Po and the negatively charged OH— may recombine to be electroneutral particle, which cannot be collected to the surface of the semiconductor detector by the electrostatic field; in such a manner that the detection efficiency is decreased. For increasing the detection efficiency, RAD7 radon monitor uses a drying tube to dry the air for reducing the air relative humidity lower than 10%; when the air relative humidity is lower than 10%, the detection efficiency is not affected; another scheme is to use the curve of temperature and humidity to revise the detection efficiency. These two methods for calibrating the detection efficiency of the radon monitor based on the electrostatic collection method both have certain limitations.

SUMMARY OF THE PRESENT INVENTION

The aim of the present invention is to provide a method and a device for measuring radon by an electrostatic collection method without an influence of an environmental temperature and an environmental humidity, for overcoming disadvantages of conventional technology that have been mentioned above.

A technical scheme of a method for measuring radon by an electrostatic collection method without an influence of an environmental temperature and an environmental humidity of the present invention is described as follows.

By reducing a pressure in an electrostatic collection and measuring chamber to below a certain threshold value, in an operation temperature range of 0-45 degrees, and an air relative humidity in an external environment changing in 0%-100%, a collection efficiency of the electrostatic collection and measuring chamber that collects positively charged $^{218}$Po particle to a surface of a semiconductor detector is basically unchanged, so when a temperature and a humidity of the external environment change, a detection efficiency does not change; the threshold value relates to a geometric factor of the measuring chamber and a distribution of an electric field intensity that in the measuring chamber.

When measuring a radon concentration by a RAD7 radon monitor, a regulating valve is installed on an inlet pipe of the measuring chamber of the RAD7 radon monitor; a sampling pump is installed on an outlet pipe of the measuring chamber; the pressure inside the measuring chamber is regulated by the regulating valve; the pressure inside the measuring chamber is reduced to 1/m atm, and then the radon concentration is measured by the electrostatic collection method; wherein, m is a rational number; according to the geometric factor and distribution conditions of the electric field intensity of different measuring chamber, the m is denoted for different value. For the measuring chamber that is used by a conventional electrostatic collection method, the pressure, the temperature, and the humidity inside the measuring chamber are same with the pressure, the temperature, and the humidity in the external environment. When the measuring chamber is in a normal temperature of 0°-45° and the air relative humidity inside a cavity of the measuring chamber is ≤x %, the detection efficiency of the measuring chamber is basically constant. A high voltage that is added between a wall of the measuring chamber and a semiconductor detector is U; a point of Q is selected randomly in the cavity of the measuring chamber; a distance that the positively charged $^{218}$Po particle drifts from the point of Q to the semiconductor detector is η; a collection time is t; an average drift velocity is V; an average collision frequency for the positively charged $^{218}$Po particle to a negatively charged ion in the air is η; the average drift velocity is much lower than a thermal motion velocity; a collision frequency is determined by the thermal motion velocity; a total collision number for the positively charged $^{218}$Po particle to the negatively charged ion in the air in the collection time t is ηt. The concentration of ion OH— is proportional to a square root of the concentration of water vapor; reducing the pressure inside the measuring chamber to 1/m atm, so the average drift velocity of the positively charged $^{218}$Po particle in any point inside the cavity of the measuring chamber is mV; the collection time changes to be t/m; the air relative humidity in the external environment is y %; the average collision frequency for the positively charged $^{218}$Po particle to the negatively charged OH— ion in the air is $\eta\sqrt{y/(mx)}$; the total collision number for the positively charged $^{218}$Po particle to the negatively charged OH— ion in the air in the collection time t is $\eta t\sqrt{y/(mx)}/m$.

When, $\eta t\sqrt{y/(mx)}/m \leq \eta t$ (1)

$$m \geq \sqrt[3]{y/x}. \quad (2)$$

Because an influence of other uncertain factors, an error range of m can be determined to be 20%.

The regulating valve regulates the pressure of the measuring chamber to satisfy a condition of the formula (2); when the air relative humidity in the external environment is 100%, the collection efficiency of the electrostatic field for collecting $^{218}$Po particle in the measuring chamber is higher or equal to the collection efficiency of an original measuring chamber; when the air relative humidity in the external environment is ≤x %, the detection efficiency of the original measuring chamber is basically constant, then the detection efficiency of a low-pressure measuring chamber is basically constant when the air relative humidity in the external environment is ≤y %; the air relative humidity is impossibly higher than 100%, thus, by regulating the pressure of the measuring chamber to satisfy the condition of the formula (2), the detection efficiency of the measuring chamber is not affected by the environmental temperature and the environmental humidity.

The present invention also provides a device for measuring radon by an electrostatic collection method without an influence of an environmental temperature and an environmental humidity, and provides a method for regulating parameters of this device when the device measures the radon concentration. The device comprises a measuring chamber, a semiconductor detector, a high-voltage module, a sampling pump, a vacuum gauge, and a regulating valve. The regulating valve is installed on an inlet pipe of the measuring chamber. The vacuum gauge and the sampling pump are installed on an outlet pipe of the measuring chamber. The semiconductor detector is installed inside an upper portion of the measuring chamber, and is connected to an interface port of the high-voltage module by a wire. Another interface port of the high-voltage module is connected to a shell of the measuring chamber by a wire.

Regulating the parameters of the device mentioned above comprises steps of:

A) opening the regulating valve and starting the sampling pump to lead into air from a radon chamber, in such fact, a humidity of the air and the radon concentration inside the measuring chamber are equal to the humidity of the air and the radon concentration in the radon chamber;

regulating an output voltage of the high-voltage module; receiving a count rate of $^{218}$Po particle decayed that is measured by the semiconductor detector by a secondary instrument, wherein when the output voltage rises, the count rate rises; when the output voltage is regulated higher continuously but the count rate is basically unchanged, stopping regulating the output voltage of the high-voltage module;

B) passing the air from the radon chamber through an efficient dryer and into the measuring chamber, in such fact, an air relative humidity in the measuring chamber is approximately zero; receiving a count rate A of the $^{218}$Po particle decayed that is measured by the semiconductor detector by the secondary instrument;

C) removing an efficient dryer, passing the air from the radon chamber through an efficient humidifier and into the measuring chamber, in such fact, the air relative humidity in the measuring chamber is 100%; regulating the regulating valve to reduce the pressure in the measuring chamber to 1/m atm; receiving the count rate of the $^{218}$Po particle decayed that is measured by the semiconductor detector by the secondary instrument; when the count rate is close to A/m, stopping regulating the regulating valve; analyzing and calculating the count rate of the $^{218}$Po particle decayed that is measured by the semiconductor detector by the secondary instrument to obtain the radon concentration; wherein at this condition, the detection efficiency of the measuring chamber is not affected by the environmental temperature and the environmental humidity.

A further technical scheme of the present invention is described as follows.

A double drying tube without a desiccant is added on an inlet pipe of a measuring chamber to pre-dry air in an entrance of the inlet pipe, and air dried is led into the measuring chamber; an air outlet of an inner wall of the double drying tube is connected to the inlet pipe of a regulating valve; an outlet pipe of the measuring chamber is connected to an air inlet port of an outer wall of the double drying tube by a pipe; wherein, the inner wall is formed by a strong water absorption material (Nafion); before the air that contains radon goes into the measuring chamber through the inner wall, because of a strong water absorption effect of the inner wall, a humidity is reduced, and the air dried that goes into the measuring chamber is sent back to the outer wall, and water vapor that is sent from the inner wall is removed by an air-vent on the outer wall. The longer the double drying tube is, the better a drying effect will be.

Regulating parameters of the device mentioned above comprises steps of:

A) removing the double drying tube, opening a regulating valve and starting a sampling pump to lead into air from a radon chamber, in such fact, a humidity of the air and a radon concentration in the measuring chamber are equal to the humidity of the air and the radon concentration in the radon chamber;

regulating an output voltage of a high-voltage module; receiving a count rate of $^{218}$Po particle decayed that is measured by a semiconductor detector by a secondary instrument, wherein when the output voltage rises, the count rate rises;

when the output voltage is regulated higher continuously but the count rate is basically unchanged, stopping regulating the output voltage of the high-voltage module;

B) passing the air from the radon chamber through an efficient dryer and into the measuring chamber, in such a manner that an air relative humidity in the measuring chamber is approximately zero;

receiving a count rate A of the $^{218}$Po particle decayed that is measured by the semiconductor detector by the secondary instrument;

C) removing an efficient dryer;
connecting to the double drying tube;
wherein after the air from the radon chamber goes through an efficient humidifier, the air having a relative humidity of 100% goes through the double drying tube and into the measuring chamber;

regulating the regulating valve to reduce a pressure in the measuring chamber to 1/m atm;

receiving the count rate of the $^{218}$Po particle decayed that is measured by the semiconductor detector by the secondary instrument;

when the count rate is close to A/m, stopping regulating the regulating valve;

analyzing and calculating the count rate of the $^{218}$Po particle decayed that is measured by the semiconductor detector by the secondary instrument to obtain the radon concentration; wherein at this condition, a detection efficiency of the measuring chamber is not affected by an environmental temperature and an environmental humidity.

Comparing with a conventional technology, the present invention has characteristics that are described as follows.

1. By regulating a pressure of a measuring chamber, the pressure of a measuring chamber satisfies a condition of a formula (2), so that a detection efficiency of the measuring chamber is not affected by an environmental temperature and an environmental humidity.

2. The present invention provides a device for measuring which has a simple structure, and is easy to use.

Referring to drawings and embodiments, the structure of the present invention is further described in detail.

These and other objectives, features, and advantages of the present invention will become apparent from the following detailed description, the accompanying drawings, and the appended claims.

DETAILED DESCRIPTION OF THE PREFERRED EMBODIMENT

Embodiment 1

Figure 1:
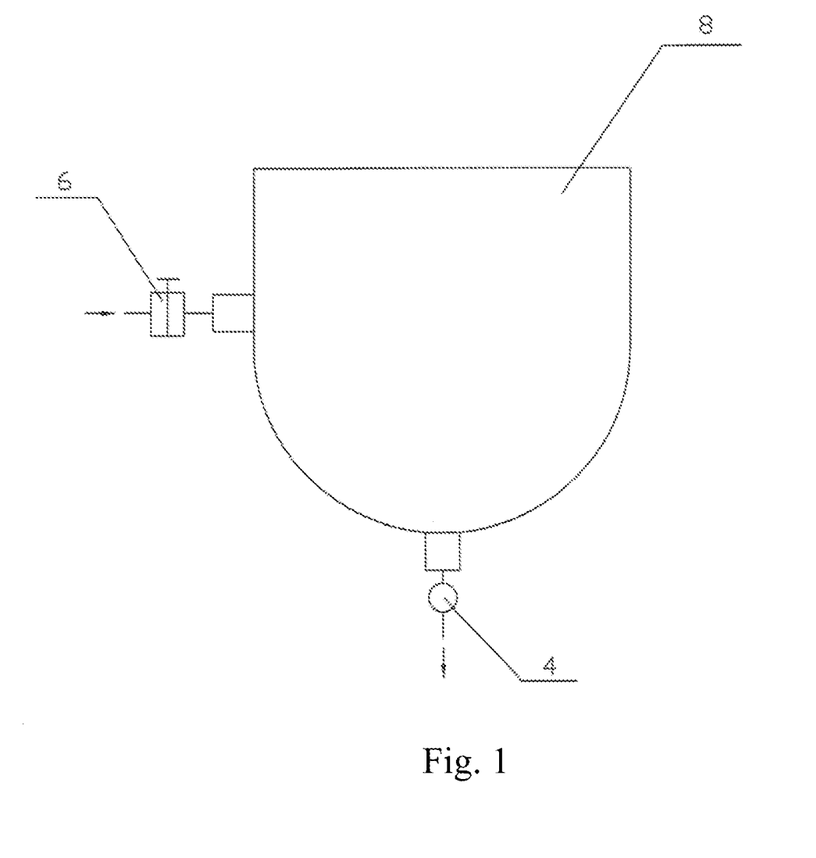
FIG. 1 is a revised structural schematic diagram of a measuring chamber of a RAD7 radon detector with a regulating valve and a sampling pump, wherein arrows indicate an air inlet and an air outlet.

A method for measuring radon by an electrostatic collection method without an influence of an environmental temperature and an environmental humidity of the present invention uses a RAD7 radon monitor to measure a radon concentration in the Embodiment 1. A measuring chamber 8 of the RAD7 radon monitor is shown by FIG. 1, wherein, a bottom of the measuring chamber 8 is a domed type, an upper part of the measuring chamber 8 is a cylindrical type, and a volume of the measuring chamber 8 is about 0.7 liters. A regulating valve 6 is set on an inlet pipe of the measuring chamber 8, and a sampling pump 4 is set on an outlet pipe of the measuring chamber 8. For the RAD7 radon monitor, under 1 atm, after an air relative humidity inside a cavity of the measuring chamber 8 is x % that is lower than 10%, a detection efficiency of the measuring chamber 8 is basically unchanged. Assuming that the air relative humidity in an external environment is y %, which is lower than 100%, inserting relevant parameters, according to a formula (2), $$m \geq \sqrt[3]{y/x} = \sqrt[3]{100/10} = 2.15$$

can be solved; i.e., a pressure inside the measuring chamber 8 is needed to be reduced to around 0.46 atm, the detection efficiency of the measuring chamber 8 is not affected by an environmental temperature and an environmental humidity. The pressure inside the measuring chamber 8 is reduced to 0.46 atm by the regulating valve 6, so that under 1 atm, an actual volume of the air inside the measuring chamber 8 is about 0.32 liters.

Embodiment 2

A method for measuring radon by an electrostatic collection method without an influence of an environmental temperature and an environmental humidity of the present invention uses a RAD7 radon monitor to measure a radon concentration in the Embodiment 2. A measuring chamber 8 of the RAD7 radon detector is shown by FIG. 1, wherein, a bottom of the measuring chamber 8 is a domed type, an upper part of the measuring chamber 8 is a cylindrical type, and a volume of the measuring chamber 8 is about 0.7 liters. A regulating valve 6 is set on an inlet pipe of the measuring chamber 8, and a sampling pump 4 is set on an outlet pipe of the measuring chamber 8. For the RAD7 radon monitor, under 1 atm, after an air relative humidity inside a cavity of the measuring chamber 8 is x % that is lower than 10%, a detection efficiency of the measuring chamber 8 is basically unchanged. Assuming that the air relative humidity in an external environment is y %, which is lower than 100%, using a pre-drying system, before the air from the external environment goes into the measuring chamber, the air relative humidity is y % that is lower than 30%. Inserting relevant parameters, according to a formula (2), $$m \geq \sqrt[3]{y/x} = \sqrt[3]{30/10} = 1.44$$

can be solved; i.e., a pressure inside the measuring chamber 8 is needed to be reduced to around 0.69 atm, the detection efficiency of the measuring chamber 8 is not affected by an environmental temperature and an environmental humidity. The pressure inside the measuring chamber 8 is reduced to 0.69 atm by the regulating valve 6, so that under 1 atm, an actual volume of the air inside the measuring chamber 8 is about 0.48 liters.

Embodiment 3

Figure 2:
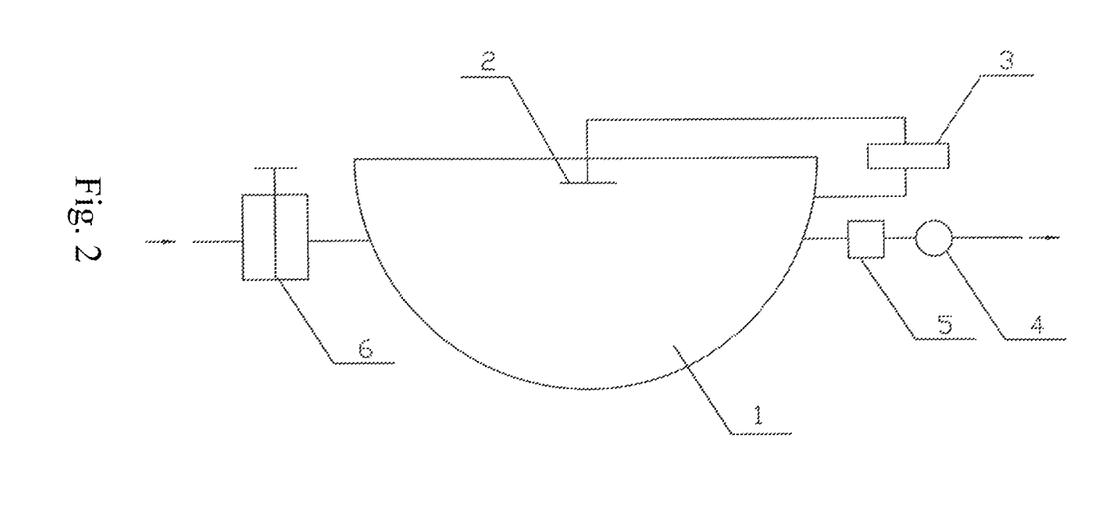
FIG. 2 is the structural schematic diagram of a device for measuring radon by an electrostatic collection method according to the present invention, wherein arrows indicate the air inlet and the air outlet.

A device for measuring radon by an electrostatic collection method without an influence of an environmental temperature and an environmental humidity comprises a measuring chamber 1, a semiconductor detector 2, a high-voltage module 3, a sampling pump 4, a vacuum gauge 5, and a regulating valve 6. The regulating valve 6 is installed on an inlet pipe of the measuring chamber 1. The vacuum gauge 5 and the sampling pump 4 are installed on an outlet pipe of the measuring chamber 1. The semiconductor detector 2 is installed inside an upper portion of the measuring chamber 1, and is connected to an interface port of the high-voltage module 3 by a wire. Another interface port of the high-voltage module 3 is connected to a shell of the measuring chamber 1 by a wire.

Regulating parameters of the device mentioned above comprises steps of:

A) opening the regulating valve 6 and starting the sampling pump 4 to lead into air from a radon chamber, in such fact, a humidity of the air and a radon concentration inside the measuring chamber 1 are equal to the humidity of the air and the radon concentration in the radon chamber;

regulating an output voltage of the high-voltage module 3;

receiving a count rate of $^{218}$Po particle decayed that is measured by the semiconductor detector 2 by a secondary instrument, wherein when the output voltage rises, the count rate rises;

when the output voltage is regulated higher continuously but the count rate is basically unchanged, stopping regulating the output voltage of the high-voltage module 3;

B) passing the air from the radon chamber through an efficient dryer and into the measuring chamber 1, in such fact, an air relative humidity in the measuring chamber 1 is approximately zero;

receiving a count rate A of the $^{218}$Po particle decayed that is measured by the semiconductor detector 2 by the secondary instrument;

C) removing an efficient dryer, passing the air from the radon chamber through an efficient humidifier and into the measuring chamber 1, in such fact, the air relative humidity in the measuring chamber 1 is 100%;

regulating the regulating valve 6 to reduce the pressure in the measuring chamber 1 to 1/m atm;

receiving the count rate of the $^{218}$Po particle decayed that is measured by the semiconductor detector 2 by the secondary instrument;

when the count rate is close to A/m, stopping regulating the regulating valve 6;

analyzing and calculating the count rate of the $^{218}$Po particle decayed that is measured by the semiconductor detector 2 by the secondary instrument to obtain the radon concentration; wherein at this condition, the detection efficiency of the measuring chamber 1 is not affected by the environmental temperature and the environmental humidity.

Embodiment 4

Figure 3:
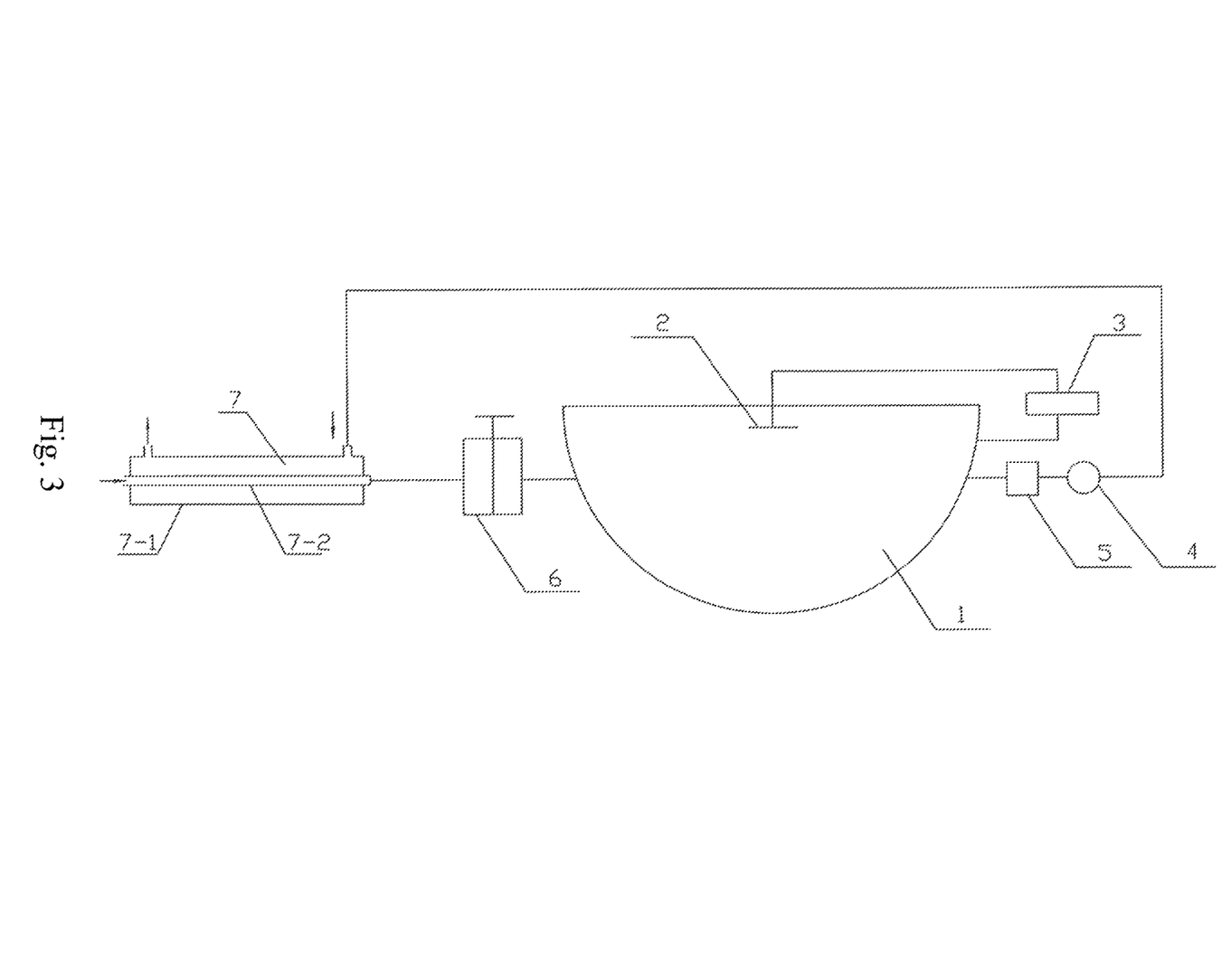
FIG. 3 is the structural schematic diagram of the device for measuring the radon by the electrostatic collection method with a double drying tube, wherein arrows indicate the air inlet and the air outlet.

A device for measuring radon by an electrostatic collection method without an influence of an environmental temperature and an environmental humidity comprises a measuring chamber 1, a semiconductor detector 2, a high-voltage module 3, a sampling pump 4, a vacuum gauge 5, a regulating valve 6, and a double drying tube 7. The regulating valve 6 is installed on an inlet pipe of the measuring chamber 1. The vacuum gauge 5 and the sampling pump 4 are installed on an outlet pipe of the measuring chamber 1. The semiconductor detector 2 is installed inside an upper portion of the measuring chamber 1, and is connected to an interface port of the high-voltage module 3 by a wire. Another interface port of the high-voltage module 3 is connected to a shell of the measuring chamber 1 by a wire. An air outlet of an inner wall 7-2 of the double drying tube 7 is connected to the inlet pipe of the regulating valve 6; an outlet pipe of the measuring chamber 1 is connected to an air inlet port of an outer wall 7-1 of the double drying tube 7 by a pipe; wherein, the inner wall 7-2 is formed by a strong water absorption material (Nafion); before the air that contains radon goes into the measuring chamber 1 through the inner wall 7-2, because of a strong water absorption effect of the inner wall 7-2, a humidity is reduced, and the air dried that goes into the measuring chamber 1 is sent back to the outer wall 7-1, and water vapor that is sent from the inner wall 7-2 is removed by an air-vent on the outer wall 7-1. The longer the double drying tube 7 is, the better a drying effect will be.

Regulating parameters of the device mentioned above comprises steps of:

A) removing the double drying tube 7, opening the regulating valve 6 and starting the sampling pump 4 to lead into the air from a radon chamber, in such fact, the humidity of the air and a radon concentration in the measuring chamber 1 are equal to the humidity of the air and the radon concentration in the radon chamber;

regulating an output voltage of the high-voltage module 3;

receiving a count rate of $^{218}$Po particle decayed that is measured by the semiconductor detector 2 by a secondary instrument, wherein when the output voltage rises, the count rate rises;

when the output voltage is regulated higher continuously but the count rate is basically unchanged, stopping regulating the output voltage of the high-voltage module 3;

B) passing the air from the radon chamber through an efficient dryer and into the measuring chamber 1, in such fact, an air relative humidity in the measuring chamber 1 is approximately zero;

receiving a count rate A of the $^{218}$Po particle decayed that is measured by the semiconductor detector 2 by the secondary instrument;

C) removing an efficient dryer;

connecting to the double drying tube 7;

wherein after the air from the radon chamber goes through an efficient humidifier, the air having a relative humidity of 100% that goes through the double drying tube 7 and into the measuring chamber 1;

regulating the regulating valve 6 to reduce a pressure in the measuring chamber 1 to 1/m atm;

receiving the count rate of the $^{218}$Po particle decayed that is measured by the semiconductor detector 2 by the secondary instrument;

when the count rate is close to A/m, stopping regulating the regulating valve 6;

analyzing and calculating the count rate of the $^{218}$Po particle decayed that is measured by the semiconductor detector 2 by the secondary instrument to obtain the radon concentration; wherein at this condition, a detection efficiency of the measuring chamber 1 is not affected by an environmental temperature and an environmental humidity.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for measuring radon, comprising steps of:
reducing a pressure in a collecting and measuring chamber of static electricity to below a certain threshold value, in an operating temperature range of 0-45 degrees, and a relative humidity of air in an external environment changing in 0%-100%, wherein a collection efficiency of the collecting and measuring chamber of the static electricity that collects positively charged $^{218}$Po particle to a surface of a semiconductor detector is basically unchanged, so when a temperature and a humidity of the external environment change, a detection efficiency does not change;

wherein the threshold value relates to a geometric factor of the measuring chamber and a distribution of an electric field intensity that in the measuring chamber.

2. The method, as recited in claim 1, further comprising a step of regulating parameters, which specifically comprises steps of:

A) opening the regulating valve and starting the sampling pump to lead into air from a radon chamber, in such fact, a humidity of the air and a radon concentration inside the measuring chamber are equal to the humidity of the air and the radon concentration in the radon chamber;

regulating an output voltage of a high-voltage module;

receiving a count rate of $^{218}$Po particle decayed that is measured by the semiconductor detector by a secondary instrument, wherein when the output voltage rises, the count rate rises;

when the output voltage is regulated higher continuously but the count rate is basically unchanged, stopping regulating the output voltage of the high-voltage module;

B) passing the air from the radon chamber through an efficient dryer and into the measuring chamber, in such fact, an air relative humidity in the measuring chamber is approximately zero;
receiving a count rate A of the $^{218}$Po particle decayed that is measured by the semiconductor detector by the secondary instrument;
C) removing the efficient dryer, passing the air from the radon chamber through an efficient humidifier and into the measuring chamber, in such fact, the air relative humidity in the measuring chamber is 100%;
regulating the regulating valve to reduce a pressure in the measuring chamber to 1/m atm;
receiving the count rate of the $^{218}$Po particle decayed that is measured by the semiconductor detector by the secondary instrument;
when the count rate is close to A/m, stopping regulating the regulating valve;
analyzing and calculating the count rate of the $^{218}$Po particle decayed that is measured by the semiconductor detector by the secondary instrument to obtain the radon concentration; wherein in this condition, a detection efficiency of the measuring chamber is not affected by an environmental temperature and an environmental humidity.

3. The method, as recited in claim 1, further comprising steps of:
when measuring a concentration of the radon by a RAD7 radon detector, installing a regulating valve on an inlet pipe of the measuring chamber of the RAD7 radon detector; installing a sampling pump on an outlet pipe of the measuring chamber;
regulating the pressure of the measuring chamber by the regulating valve; wherein, the pressure inside the measuring chamber is reduced to 1/m atm, and then the concentration of the radon is measured by the electrostatic collection method;
wherein, m is a rational number; according to different geometric factor of the measuring chamber, and different distribution conditions of different electric field intensity inside the measuring chamber, the m is denoted for different value; for the measuring chamber that is used by a conventional electrostatic collection method, the pressure, the temperature, and the humidity inside the measuring chamber are same with the pressure, the temperature, and the humidity in the external environment; when the measuring chamber is in a normal temperature of 0°-45° and the relative humidity of the air inside a cavity of the measuring chamber is ≤x %, the detection efficiency of the measuring chamber is basically constant; a voltage of a high voltage that is added between the cavity of the measuring chamber and a semiconductor detector is U; a point of Q is selected randomly in the cavity of the measuring chamber; a distance that the positively charged $^{218}$Po particle drifts from the point of Q to the semiconductor detector is L; a collection time is t; an average drift velocity is V; an average collision frequency for the positively charged $^{218}$Po particle to collide with negatively charged ion in the air is the average drift velocity is much lower than a thermal motion rate; a collision frequency is determined by the thermal motion rate; a total number for the positively charged $^{218}$Po particle to collide with the negatively charged ion in the air in the collection time t is lit; the concentration of ion OH— is proportional to a square root of the concentration of water vapour; reducing the pressure inside the measuring chamber to 1/m atm, so the average drift velocity of the positively charged $^{218}$Po particle in any point inside the cavity of the measuring chamber is mV; the collection time changes to be t/m; the relative humidity of the air in the external environment is y %; the average collision frequency for the positively charged $^{218}$Po particle to collide with the ion OH— of the negatively charged ion in the air is $\eta\sqrt{y/(mx)}$; the total number for the positively charged $^{218}$Po particle to collide with the ion OH— of the negatively charged ion in the air in the collection time t is $\eta t\sqrt{y/(mx)}/m$;

when, $\eta t\sqrt{y/(mx)}/m \leq \eta t$ \hfill (1)

$$m \geq \sqrt[3]{y/x} ;$$ \hfill (2)

because the influence of other uncertain factors, an error range of m can be determined to be 20%;
the regulating valve regulates the pressure of the measuring chamber to satisfy a condition of the formula (2) by the regulating valve; wherein, when the relative humidity of the air in the external environment is 100%, the collection efficiency of the electrostatic field collecting $^{218}$Po particle in the measuring chamber is higher or equal to the collection efficiency of a original measuring chamber; when the relative humidity of the air in the external environment is ≤x %, the detection efficiency of the original measuring chamber is basically constant; when the relative humidity of the air in the external environment is ≤y %, the detection efficiency of a low-pressure measuring chamber is basically constant; the relative humidity of the air is impossibly higher than 100%; thus, regulating the pressure of the measuring chamber to satisfy the condition of the formula (2), the detection efficiency of the measuring chamber is not affected by the environmental temperature and the environmental humidity.

4. A device for measuring radon, comprising a measuring chamber, a semiconductor detector, a high-voltage module, a sampling pump, a vacuum gauge, and a regulating valve; wherein, said regulating valve is installed on an inlet pipe of said measuring chamber; said vacuum gauge and said sampling pump are installed on an outlet pipe of said measuring chamber; said semiconductor detector is installed inside an upper portion of said measuring chamber, and is connected to an interface port of said high-voltage module by a wire; another interface port of said high-voltage module is connected to a shell of said measuring chamber by a wire;
wherein, a double drying tube without a desiccant is added on said inlet pipe of said measuring chamber to pre-dry air in an entrance of said inlet pipe, and air dried is led into said measuring chamber; an air outlet of an inner wall of said double drying tube is connected to said inlet pipe of said regulating valve; said outlet pipe of said measuring chamber is connected to an air inlet port of an outer wall of said double drying tube by a pipe.

5. The method, as recited in claim 3, further comprising a step of regulating parameters, which specifically comprises steps of:
A) removing the double drying tube, opening the regulating valve and starting a sampling pump to lead into air from a radon chamber, in such fact, a humidity of the air and a radon concentration in the measuring chamber are equal to the humidity of the air and the radon concentration in the radon chamber;

regulating an output voltage of a high-voltage module;

receiving a count rate of $^{218}$Po particle decayed that is measured by a semiconductor detector by a secondary instrument, wherein when the output voltage rises, the count rate rises;

when the output voltage is regulated higher continuously but the count rate is basically unchanged, stopping regulating the output voltage of the high-voltage module;

B) passing the air from the radon chamber through an efficient dryer and into the measuring chamber, an air relative humidity in the measuring chamber is approximately zero;

receiving a count rate A of the $^{218}$Po particle decayed that is measured by the semiconductor detector by the secondary instrument;

C) removing an efficient dryer;

connecting to the double drying tube;

wherein after the air from the radon chamber goes through an efficient humidifier, the air having a relative humidity is 100% goes through the double drying tube and into the measuring chamber;

regulating the regulating valve to reduce a pressure in the measuring chamber to 1/m atm;

receiving the count rate of the $^{218}$Po particle decayed that is measured by the semiconductor detector by the secondary instrument;

when the count rate is close to A/m, stopping regulating the regulating valve;

analyzing and calculating the count rate of the $^{218}$Po particle decayed that is measured by the semiconductor detector by the secondary instrument to obtain the radon concentration; wherein in this condition, a detection efficiency of the measuring chamber is not affected by an environmental temperature and an environmental humidity.

* * * * *